United States Patent [19]

Biedermann et al.

[11] Patent Number: 4,505,854
[45] Date of Patent: Mar. 19, 1985

[54] OPTICALLY ACTIVE DIPEPTIDES AND THE USE THEREOF AS TISSUE DISSOLVING AND HISTOLYTIC AGENT IN HUMAN BEINGS

[75] Inventors: Jürgen Biedermann, Pulheim-Stommeln; Eugen Etschenberg, Cologne; Hugo Friehe, Erftstadt-Lechenich; Wolfgang Scheef, Bonn; Johannes Winkelmann, Cologne, all of Fed. Rep. of Germany

[73] Assignee: Nattermann & Cie GmbH, Cologne, Fed. Rep. of Germany

[21] Appl. No.: 568,287

[22] Filed: Jan. 5, 1984

Related U.S. Application Data

[63] Continuation of Ser. No. 397,089, Jul. 12, 1982, abandoned.

[30] Foreign Application Priority Data

Jul. 15, 1981 [DE] Fed. Rep. of Germany ....... 3127930

[51] Int. Cl.³ .......................................... C07C 103/52
[52] U.S. Cl. ............................................. 260/112.5 R
[58] Field of Search .................. 260/112.5 R; 424/177

[56] References Cited

U.S. PATENT DOCUMENTS 4,310,517  1/1982  Etschenberg et al. .............. 424/177

FOREIGN PATENT DOCUMENTS 2901667  7/1980  Fed. Rep. of Germany ... 260/112.5 R

Primary Examiner—Delbert R. Phillips
Attorney, Agent, or Firm—Pearne, Gordon, Sessions, McCoy, Granger & Tilberry

[57] ABSTRACT

The invention relates to the new optically active dipeptide D-2-phenylglycyl-D-2-phenylglycine and its pharmacologically acceptable salts or acid addition salts and the use thereof as tissue dissolving and histolytic agent.

2 Claims, No Drawings

OPTICALLY ACTIVE DIPEPTIDES AND THE USE THEREOF AS TISSUE DISSOLVING AND HISTOLYTIC AGENT IN HUMAN BEINGS

This is a continuation of application Ser. No. 397,089, filed on July 12, 1982 now abandoned.

The present invention relates to the new optically active dipeptide D-2-phenylglycyl-D-2-phenylglycine and its pharmacologically acceptable salts and acid addition salts, and to the use of these compounds as tissue-dissolving and histolytic medicaments.

The tissue dissolving and histolytic action of various substances is known per se, for instance from compounds of quite different structures, such as, for example, adriamycin, bleomycin, vinblastine, vincristine, cisplatin and the oxazaphosphorins cyclophosphamide and ifosfamide. Those compounds, however, in addition to partial success, have side effects which are still very pronounced, such as, for example, anorexia, diarrhoea, leucopenia, thrombocytopenia, nausea, vomiting and loss of hair. Although successful attempts to reduce the side effects have recently been undertaken, such as, for example, combination of oxazaphosphorins with mesna, a mercaptoethylsulphonic acid, the discovery of new substances which are better tolerated by the organism and have a direct or indirect action as tissue-dissolving and histolytic products is still of top priority.

German Offenlegungsschrift No. 2,901,667 proposes dipeptides of essential aminoacids. However, the toxicity of these compounds of 300 mg/kg when administered intravenously (to rodents) is still quite high. The same publication mentions the use of dehydrooligopeptides of low toxicity (U.S. Pat. No. 4,310,517), but these have some disadvantages. In the animal experiment reproduced, these disadvantages of the dehydrooligopeptides have been recognised as the induction of severe pain conditions in the experimental animals.

Surprisingly, it has now been found that the new optically active dipeptide D-2-phenylglycyl-D-2-phenylglycine is a substance having a toxicity which is 3 times lower, coupled with outstanding properties to induce necrosis and activate macrophages. This is all the more surprising since, of the 9 possibilities of combining D-, L- and DL-2-phenylglycine to give dipeptides, the racemate DL-2-phenylglycyl-DL-2-phenylglycine (sic), which is obtained, in addition to 2,5-dimethyl-3,6-diphenyl-pyrazine, when (±)-2-morpholino-1-phenylpropan-1-one hydrochloride is heated to 105° C. with potassium cyanide and ammonium carbonate in aqueous ethanol (Craig W. C. and Henze H. R., J. Org.-Chem. 10 (1945), 10–15), has only a very low activity, and L-2-phenylglycyl-L-2-phenylglycine has no activity.

From the findings of the investigations, the compound D-2-phenylglycyl-D-2-phenylglycine hydrochloride according to the invention is most suitable as products with tissue-dissolving and histolytic activity. The present invention relates to D-2-phenylglycyl-D-2-phenylglycine and its pharmaceutically acceptable salts and acid addition salts, such as, for example, its dihydrogen phosphate and hydrogen sulphate. D-2-Phenylglycyl-D-2-phenylglycine hydrochloride and D-2-phenylglycyl-D-2-phenylglycine (sic) hydrobromide, especially the hydrochloride, are particularly singled out and preferred.

The compound according to the invention is prepared in a manner which is known per se, by the conventional methods customary in peptide chemistry, such as, for example, the azide method, by the method of mixed anhydrides, by the carbodiimide method, by the method of active esters, which has numerous variants, or by the silyl ester method (cf. the review: E. Wünsch (1974), Synthese von Peptiden (Synthesis of Peptides), Houben-Weyl, Methoden der organischen Chemie (Methods of Organic Chemistry), Volumes 15/1 and 15/2).

One variant of the active ester method according to Birkofer et al. leads to the desired end product virtually in the absence of racemisation (Birkofer L. and Ritter, A.: Die Silylierung als Hilfsmittel in der organischen Synthese (Silylation as an aid in organic synthesis), in: Neuere Methoden der präparativen organischen Chemie (Recent methods of preparative organic chemistry), Volume II, pages 185–209). In contrast, dipeptide synthesis using an N-protected D-2-phenylglycine and D-2-phenylglycine methyl ester by the method of mixed anhydrides leads to complete racemisation at the necessary stage of ester hydrolysis.

The present invention furthermore relates to pharmaceutical products which contain the compound of the formula I or a salt or acid addition salt. The pharmaceutical products according to the invention are for enteral, such as oral or rectal, or parenteral administration and contain the pharmacological active compounds by themselves or together with a conventional pharmaceutically usable excipient. The compounds according to the invention, in particular the dipeptide hydrochloride, can be used in the form of injectable solutions, in particular for local administration.

The pharmaceutical formulation of the active compound is advantageously in the form of individual doses corresponding to the desired administration, such as, for example, tablets, coated tablets, capsules, suppositories, granules, emulsions or suspensions. Such solutions are preferably aqueous solutions, and these products, which are lyophilised, for example, and contain the active substance by itself or together with an excipient, can be prepared before use. The dosage is between 1 and 1,000 mg/dose, preferably 200–400 mg/dose.

After local administration, for example into healthy guineapig skin, massive infiltration of macrophages and giant cells is observed at the administration site. Local and sharply delineated histolysis is the result. Histolysis with an intact skin surface is also observed. It is remarkable that no indications of general intolerance are observed. The $LD_{50}$ of the compound according to the invention in an acute experiment is 1,000 mg/kg when administered intravenously (to rodents). To demonstrate the specifically histolytic action of the compound according to the invention, D-2-phenylglycyl-D-2-phenylglycine was administered once under the shaven dorsal skin of guineapigs. The dosages were 25 or 50 mg/animal. As a comparison for the 25 mg dose, glycine hydrobromide (10.7 mg/animal), as a control, and the racemate DL-2-phenylglycyl-DL-2-phenylglycine (25 mg/animal) were used.

The animals were observed for clinical and local changes for 7 days. They were then autopsied and the injection sites (skin and muscle) were subjected to pathological-anatomical and pathological-histological evaluation.

Injection of the compounds according to the invention causes histolysis as a result of a high degree of macrophage and giant cell infiltration. This is a chemotactic and activating action on macrophages, which also has a tissue dissolving effect. No systemic toxic symptoms or clinically detectable changes could be observed in any of the experimental animals. In contrast, administration of the control compound or of the racemate causes no local changes.

The invention will be described in more detail with the aid of the following examples:

EXAMPLE 1

Preparation of D-2-phenylglycyl-D-2-phenylglycine hydrobromide

N-Benzyloxycarbonyl-D-2-phenylglycine, melting point: 134° C., $[\alpha]_D^{20} = -110.9°$ (c=1/MeOH) is reacted with 4-nitrophenyol (sic) in the presence of N,N'-dicyclohexylcarbodiimide in tetrahydrofuran at +4° C. to give the nitrophenyl ester, melting point: 102° C., $[\alpha]_D^{20} = -66.2°$ (c=1/MeOH). The nitrophenyl ester is fused with N-trimethylsilylacetamide and D-2-phenylglycine at between 60° C. and 100° C. to give the N-benzyloxycarbonyl-dipeptide silyl ester, and working up gives N-benzyloxycarbonyl-D-2-phenylglycyl-D-2-phenylglycine, melting point: 210° C., $[\alpha]_D^{20} = -90.3°$ (c=1/DMF). Demasking is effected with HBr/glacial acetic acid, and leads to D-2-phenylglycyl-D-2-phenylglycine hydrobromide, melting point from 175° C. (decomposition), $[\alpha]_D^{20} = -111.7°$ (c=1/H$_2$O), $C_{16}H_{16}N_2O_3 \cdot HBr$ [365.2].

EXAMPLE 2

Preparation of D-2-phenylglycyl-D-2-phenylglycine hydrochloride

Stage 1

N-tert.-Butoxycarbonyl-D-2-phenylglycine 75.6 g=0.5 mol of D-2-phenylglycine, melting point: 302° C. (decomposition), $[\alpha]_D^{20} = -154.4°$ (c=1/1N HCl) are dissolved in a solution of 20 g (=0.5 mol) of NaOH in 500 ml of water, the solution is cooled to +4° C. in an ice-water bath and a solution of 120.1 g (=0.55 mol) of di-tert.-butyl dicarbonate in 1,000 ml of dioxane is added, with stirring. When the addition of the di-tert.-butyl dicarbonate has ended, the mixture is subsequently stirred at room temperature for a further 10 hours, until the evolution of CO$_2$, monitored by a bubble counter, has ended. After the contents of the flask have been acidified to pH 2 with dilute hydrochloric acid, the N-tert.-butoxycarbonyl-D-2-phenylglycine is extracted with ethyl acetate and the ethyl acetate phase is extracted 3 times by shaking with 100 ml of water. The organic phase is then dried over Na$_2$SO$_4$ and filtered, and the filtrate is concentrated in vacuo. An oil remains, a small sample of which is induced to crystallise with petroleum ether (40°–60° C.). Petroleum ether and the seed crystals are now added to the main portion, and the mixture is stirred vigorously. Crystallisation is complete after a short time. The crystals are filtered off with suction and dried in vacuo to give 112.4 g (=89.5% of theory) of N-tert.-butoxycarbonyl-D-2-phenylglycine, melting point: 90°–91° C., $[\alpha]_D^{20} = -129.2°$ (c=1/DMF), $C_{13}H_{17}NO_4$ [251.3].

Stage 2

N-tert.-Butoxycarbonyl-D-2-phenylglycine 4-nitrophenyl ester 125.7 g (=0.5 mol) of N-tert.-butoxycarbonyl-D-2-phenylglycine are dissolved in 800 ml of tetrahydrofuran together with 69.6 g (=0.5 mol) of 4-nitrophenol. After the contents of the flask have been cooled to +4° C. in an ice-water bath, a solution of 103.2 g (=0.5 mol) of dicyclohexylcarbodiimide in 100 ml of tetrahydrofuran is added, whilst stirring, and the mixture is allowed to come to room temperature and is subsequently stirred for about 12 hours. The dicyclohexylurea which has precipitated is filtered off with suction, the filtrate is concentrated in vacuo and the solidified residue is extracted by stirring with di-iso-propyl ether. The substance is filtered off with suction and dried in vacuo to give 140.6 g (=75.5% of theory) of N-tert.-butoxycarbonyl-D-2-phenylglycine 4-nitrophenyl ester. $C_{19}H_{20}N_2O_6$ [372.4], melting point: 159°–160° C., $[\alpha]_D^{20} = -81,5°$ (sic) (c=1/THF).

Stage 3

N-tert.-Butoxycarbonyl-D-2-phenylglycyl-D-2-phenylglycine 223.4 g (=0.6 mol) of N-tert.-butoxycarbonyl-D-2-phenylglycine 4-nitrophenyl ester, 236 g (=1.8 mols) of N-trimethylsilylacetamide and 90.7 g (=0.6 mol) of D-2-phenylglycine are fused at a bath temperature of 60°–80° C. in the absence of atmospheric moisture, and the mixture is then stirred at this temperature for a further 14 hours. After cooling, the solidified melt is taken up in ethyl acetate and the ethyl acetate extract is extracted by shaking with saturated aqueous KHCO$_3$ solution. Desilylation is thereby effected, and the potassium salt of the N-tert.-butoxycarbonyl-dipeptide acid dissolves in the aqueous phase. The aqueous phase is separated off and, after being acidified to pH 2 with dilute hydrochloric acid, is extracted by shaking with fresh ethyl acetate and the ethyl acetate phase is washed twice with small amounts of water and dried briefly over Na$_2$SO$_4$. The Na$_2$SO$_4$ is filtered off and the filtrate is treated with the same amount of petroleum ether (40°–60°). The N-tert.-butoxycarbonyl-dipeptide acid which has crystallised out is filtered off with suction and dried in vacuo. Yield: 170.6 g (=74% of theory) of N-tert.-butoxycarbonyl-D-2-phenylglycyl-D-2-phenylglycine. $C_{21}H_{24}N_2O_5$ [384.4], melting point: 101° C., $[\alpha]_D^{20} = -111.3°$ (c=1/DMF).

Stage 4

D-2-Phenylglycyl-D-2-phenylglycine hydrochloride 71.0 g (=0.185 mol) of N-tert.-butoxycarbonyl-D-2-phenylglycyl-D-2-phenylglycine are suspended in 150 ml of glacial acetic acid, and 300 ml of a saturated solution of HCl in glacial acetic acid are added at room temperature, whilst stirring. The N-tert.-butoxycarbonyldipeptide acid thereby dissolves immediately. Shortly afterwards, crystallisation of the demasked peptide in the form of the dipeptic hydrochloride starts. After about 3 hours, the non-hygroscopic salt is filtered off with suction, washed with absolute ether and recrystallised twice from methanol/ether. The substance is dried to constant weight at a bath temperature of 50° C. under an oil pump vacuum and is then dissolved in double distilled water (4% strength), sterilised by filtration and lyophilised.

Yield: 48.2 g (=81.2% of theory) of D-2-phenylglycyl-D-2-phenylglycine hydrochloride. $C_{16}H_{16}N_2O_3 \cdot HCl$ [320.8], melting point: 175° C. (decomposition), $[\alpha]_D^{20} = -124.1$ (c=1/water).

Mass spectrum, Varian MAT-311-A (70 eV): M$^+$-18 ($C_{16}H_{14}N_2O_2{}^+$): m/z 266; M$^+$-46 ($C_{15}H_{14}N_2O^+$): m/z 238; $M^+-61$: m/z 223; $C_8H_6O^+$: m/z 118; $C_7H_8N^+$: m/z 106; $C_6H_5^+$: m/z 77; and $HCl^+$: m/z 36 and 38.

EXAMPLE 3

A 4% strength aqueous solution of D-2-phenylglycyl-D-2-phenylglycine hydrochloride in double-distilled water is sterilised by filtration, lyophilised and 100 mg, 200 mg and 400 mg portions of the lyophilisate are filled into ampoules under sterile conditions.

EXAMPLE 4

50 mg of D-2-phenylglycyl-D-2-phenylglycine hydrochloride, 150 mg of microcrystalline cellulose, 50 mg of Aerosil, 15 mg of Cutina HR and 20 mg of hydroxymethylcellulose phthalate. The substances listed are mixed, the mixture is pressed and the pressed tablets are coated with a film of hydroxymethylcellulose phthalate.

EXAMPLE 5

100 mg of D-2-phenylglycyl-D-2-phenylglycine hydrochloride, 5 mg of talc and 10 mg of Aerosil 200 are mixed, the mixture is granulated and the granules are filled into hard gelatine capsules.

What we claim is:

1. The optically active dipeptide D-2-phenylglycyl-D-2-phenylglycine of the formula I

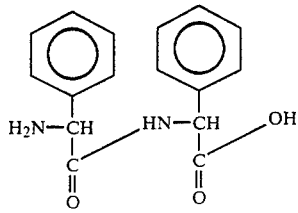

and its pharmaceutically acceptable salts and acid addition salts.

2. D-2-Phenylglycyl-D-2-phenylglycine hydrobromide and hydrochloride.

* * * * *